United States Patent [19]

Damo et al.

[11] Patent Number: 5,371,105
[45] Date of Patent: Dec. 6, 1994

[54] AQUEOUS FORMULATIONS AND THEIR USE

[75] Inventors: Zoltan Damo, Eppstein, Germany; Ernst Neuenschwander, Riehen, Switzerland

[73] Assignee: Hoechst Aktiengesellschaft, Frankfurt am Main, Germany

[21] Appl. No.: 936,817

[22] Filed: Aug. 27, 1992

Related U.S. Application Data

[63] Continuation of Ser. No. 648,497, Jan. 30, 1991, abandoned, which is a continuation of Ser. No. 399,203, Aug. 28, 1989, abandoned.

[30] Foreign Application Priority Data

Sep. 2, 1988 [CH] Switzerland .................. 3282/88

[51] Int. Cl.$^5$ ............................................. A61K 31/34
[52] U.S. Cl. ................................... 514/469; 514/492
[58] Field of Search .......................... 514/469, 492

[56] References Cited

U.S. PATENT DOCUMENTS

| | | | |
|---|---|---|---|
| 3,317,612 | 5/1967 | Nunn et al. | 260/613 |
| 4,044,118 | 8/1977 | McCoy et al. | 424/200 |
| 4,319,918 | 3/1982 | Baltruschat et al. | 71/118 |
| 4,460,406 | 7/1984 | Valange | 71/100 |
| 4,624,679 | 11/1986 | McEntee | 8/650 |
| 4,886,656 | 12/1989 | Obayashi et al. | 424/10 |

FOREIGN PATENT DOCUMENTS

| | | |
|---|---|---|
| 47-24128 | 7/1972 | Japan . |
| 56-75409 | 6/1981 | Japan . |
| 01-9901 | 1/1989 | Japan . |
| 1583713 | 1/1991 | United Kingdom . |

OTHER PUBLICATIONS

Ceauseacu et al, Chem. Abs. 108:76916x (1988).
Goldenberg et al, Chem. Abs. 111:92347c (1989).
Pussemier, Chem. Abs. 110:19826K (1989).
Andrews et al, Chem. Abs. 90:198241d (1979).
Diery et al, Chem. Abs. 99:6912z (1983).
Merck Index, No. 1521, pp. 215–216.
McCutcheon's Detergents & Emulsifiers 1973 N. American Edition 1974.
Pandele et al 110 CA:26491a 1987.
Pandele et al 103 CA:216710z 1985.
Luca et al 108 CA:170640z 1988.
Obayashi et al 105 CA:221052g 1986.
Nunn et al 67 CA:23143w 1967.
Morton Thiokol 106 CA:133787r 1987.

*Primary Examiner*—Marianne M. Cintins
*Assistant Examiner*—Russell Travis

[57] ABSTRACT

The invention relates to aqueous formulations containing 1 to 70% by weight of an agrochemical active substance which is sparingly soluble in water, besides an amount which inhibits crystallization of the active substance or breaking of the emulsion, of a compound of the formula I $$R\text{—}O\text{—}M \qquad (I),$$

where
- R is $C_{12}$–$C_{20}$alkyl; $C_{12}$–$C_{20}$alkenyl; phenyl; 4-biphenylyl; phenyl which is disubstituted to trisubstituted by α-methylbenzyl or α-methyl-4-methylbenzyl; or phenyl which is monosubstituted to trisubstituted by alkyl, the total of the carbon atoms in the alkyl groups being 1 to 18; and
- M is hydrogen; a cation equivalent of an alkai metal ion or alkaline earth metal ion; or, in the event that R is phenyl, 4-biphenylyl or phenyl which is substituted by α-methylbenzyl, α-methyl-4-methylbenzyl or alkyl, M can also be ammonium, monoethanolammonium or diethanolammonium;

and, if desired, other formulation auxiliaries and/or further agrochemical active substances and their use as seed-dressing agents.

3 Claims, No Drawings

AQUEOUS FORMULATIONS AND THEIR USE

This is a continuation of Ser. No. 07/648,497 filed Jan. 30, 1991, now abandoned which is a continuation of Ser. No. 07/399,203 filed Aug. 28, 1989, now abandoned.

The present invention relates to novel aqueous formulations of agrochemical active substances which are sparingly soluble in water. These novel formulations are either water-in-oil or oil-in-water emulsions. The novel formulations can advantageously be used as seed-dressing agents.

Emulsions which contain active substances of the above described type, which are only sparingly soluble in water, tend to crystallize or to break (separate) the emulsion upon standing for a substantial period of time and are therefore storage-stable and stable on use for a limited period only.

It has now been found that the formation of crystals, or even the breaking of aqueous emulsions, in active substances which are sparingly soluble in water can be prevented, and the shelf-life can therefore be improved, when these active substances are converted into aqueous formulations with the aid of the compounds described below. In the case of the active compound furathiocarb (O-butyl O-2,3-dihydro-2,2-dimethyl-benzofuran-7-yl N,N'-dimethyl-N,N'-thiodicarbamate), for example, aqueous formulations of the conventional type have a pronounced tendency to form crystals of this active substance.

The invention therefore relates to aqueous formulations which contain 1 to 70, preferably 2 to 70, % by weight of an agrochemical active substance which is sparingly soluble in water, besides an amount which inhibits crystallization of the active substance or breaking of the emulsion, of a compound of the formula I

R—O—M  (I), where
R is $C_{12}$–$C_{20}$alkyl; $C_{12}$–$C_{20}$alkenyl; phenyl; 4-biphenylyl; phenyl which is disubstituted to trisubstituted by α-methylbenzyl or α-methyl-4-methylbenzyl; or phenyl which is monosubstituted to trisubstituted by alkyl, the total of the carbon atoms in the alkyl groups being 1 to 18; and
M is hydrogen; a cation equivalent of an alkali metal ion or alkaline earth metal ion; or, in the event that R is phenyl, 4-biphenylyl or phenyl which is substituted by α-methylbenzyl, α-methyl -4-methylbenzyl or alkyl, M can also be ammonium, monoethanolammonium or diethanolammonium;
and, if desired, other formulation auxiliaries and/or further agrochemical active substances.

Formulation auxiliaries which are customary in agrochemical formulations are, inter alia, emulsifiers, dispersants, thickeners, antifoam agents, stabilizers, colorants, tackifiers, preservatives, buffers and low-temperature stabilizers.

Agrochemical active substances are in particular herbicides, fungicides, insecticides, acaricides, gametocides, rodenticides, nematicides, growth regulators and safeners. Agrochemical active substances which are considered as sparingly soluble in water are those of which less than 1% is soluble in water at 20° C.

The formulation type suggested according to the invention is advantageously suitable for agrochemical active substances which have a melting point in the range of −5° C. to +70° C.

This means that active substances which are suitable are substances which are liquid at room temperature as well as substances which are solid at room temperature. However, the problem of the active substances crystallizing even occurs with those active substances which are liquid at room temperature (temperatures of below 40° C.), since agrochemical formulations also have to have low-temperature stability at lower temperatures (for example storage in unheated rooms).

Agrochemical active substances are in particular the insecticide furathiocarb (butyl 2,3-dihydro-2,2-dimethyl-benzofuran-7-yl N,N'-dimethyl-N,N'-thiodicarbamate), which is described in "The Pesticide Manual, 7th Ed. The British Crop Prot. Counc. (Ed), 6850" and in British Patent Specification 1,583,713. Other suitable active substances are the insecticides Methidathion (S-2,3-dihydro-5-methoxy-2-oxo-1,3,4-thiadiazol-3-ylmethyl O,O-dimethyl dithiophosphate; Pesticide Manual, 8th Ed. 1987, page 546) and the herbicide Trimexachlor (N-chloroacetyl-N-isopropyl-3,3,5-trimethylcyclohex-1-enamine, described in EP-A-0,013,429).

By virtue of their chemical structure, the compounds of the formula I correspond to phenols or saturated or unsaturated alcohols.

From the group of the phenols, preferred sub-groups are those mentioned below:
a) phenol
b) 4-hydroxybiphenylyl
c) phenols which are monosubstituted to trisubstituted by ($C_1$–$C_6$)alkyl groups; for example monobutylphenol, dibutylphenol or tributylphenol; the sec-butylphenols, such as mono-sec-butylphenol, di-sec-butylphenol or tri-sec-butylphenol are particularly preferred,
d) phenols which are monosubstituted by a ($C_6$–$C_{18}$)alkyl group; for example nonylphenol, octylphenol or dodecylphenol,
e) phenols which are disubstituted by ($C_4$–$C_9$)alkyl groups; for example dinonylphenol or dioctylphenol,
f) phenols which are disubstituted or trisubstituted by α-methylbenzyl or α-ethyl-4-methylbenzyl; for example 2,4,6-tris-[α-methylbenzyl]phenol or 2,4,6-tris-[α-methyl-4-methylbenzyl]phenol.

Preferred alcohols from the group of the saturated and unsaturated alcohols are primary saturated alcohols or primary ($C_{12}$–$C_{20}$)alcohols which are monounsaturated to triunsaturated, i.e. fatty alcohols, for example oleyl alcohol, lauryl alcohol or stearyl alcohol.

Depending on the preparation methods, the fatty alcohols can also be present as a mixture of various alcohols, for example coconut fatty alcohol.

The compounds of the formula I can also be present for example in the form of their alkali metal salts or alkaline earth metal salts (for example in the form of the Li, Na, K, Ca or Mg salts) or, in the case of the phenols, also in the form of their ammonium salts or other amine salts (for example in the form of the monoethanolammonium or diethanolammonium salts).

The salts of the formula I (in which M is not hydrogen) can also be present in mixtures with other salts of compounds of the formula I or also in mixtures with alcohols or phenols of the formula I (in which M represents hydrogen).

The minimum amount of compounds I required for preventing crystallization of the agrochemical active substances can be determined by simple experiments.

The weight ratio of agrochemical active substance to the compound of the formula I is advantageously 20:1 to 3:1, in particular 10:1 to 5:1.

The agrochemical active substances can advantageously be first dissolved with the compounds of the formula I and then dispersed in the aqueous phase. Active substances which are solid at room temperature are liquefied by heating (before or after admixing the compound of the formula I).

It has been found that the compounds of the formula I also have a certain emulsifying effect in aqueous agrochemical formulations.

This means that, as a further advantageous effect, the amount of formulation auxiliaries in agrochemical formulations can be reduced when compounds of the formula I are used.

Besides the compounds of the formula (I) mentioned at the outset, the formulations according to the invention can also additionally contain emulsifiers. Non-ionic or anionic emulsifiers in amounts of 0.1–10% by weight, preferably 0.5–5% by weight, are preferred.

Suitable anionic emulsifiers can be so-called water-soluble soaps, as well as water-soluble synthetic surface-active compounds.

Soaps are the alkali metal salts, alkaline earth metal salts or substituted or unsubstituted ammonium salts of higher fatty acids ($C_{10}$–$C_{22}$), for example the Na or K salts of oleic or stearic acid, or of natural mixtures of fatty acids which can be obtained for example from coconut oil or tallow oil.

However, so-called synthetic emulsifiers are used more frequently, in particular fat sulphonates, fat sulphates, sulphonated benzimidazole derivatives or alkylarylsulphonates, for example calcium dodecylbenzene-sulphonate.

Suitable non-ionic emulsifiers are mainly polyglycol ether derivatives of aliphatic or cycloaliphatic alcohols, of saturated or unsaturated fatty acids and of alkylphenols, which can contain 3 to 10 glycol ether groups and 8 to 20 carbon atoms in the (aliphatic) hydrocarbon radical and 6 to 18 carbon atoms in the alkyl radical of the alkylphenols.

Examples of non-ionic emulsifiers are nonylphenol polyethoxyethanols, castor oil polyglycol ethers, polypropylene/polyethylene oxide adducts, tributylphenoxy polyethoxyethanol, polyethylene glycol and octylphenoxy polyethoxyethanol.

Possible additives which can also be contained in the formulations according to the invention are preservatives, colorants, buffers, low-temperature stabilizers and agents for improving the chemical stability of the active substance. Examples of preservatives are 2-hydroxybiphenyl and sorbic acid. Examples of colorants are azo dyes and phthalocyanine pigments. Buffer substances are sodium dihydrogen phosphate, ammonium acetate or diammonium phosphate. Examples of low-temperature temperature stabilizers are preferably glycerol, but also urea, ethylene glycol, propylene glycol, polyglycols and various sugars and salts, such as ammonium sulphate and sodium oleate. These low-temperature stabilizers can be present in the emulsion according to the invention in amounts of 2 to 20, preferably 5 to 15, % by weight. The crystallization inhibitors are added to aqueous formulations for improving the low-temperature stability of the aqueous phase, while the compounds of the formula I effect, inter alia, an improvement of the low-temperature stability of the emulsified organic phase. Tackifiers are, inter alia, aqueous polymer suspensions, for example latex suspensions.

The formulations according to the invention in their general form are prepared in such a way that a mixture of active substance and compound of the formula (I) is emulsified in the required amount of water, with stirring. If the formulation is to additionally contain further substances of the abovementioned type, the water-soluble substances are generally first dissolved in the required amount of water. To this stirred mixture is then added the mixture of all components which are not soluble in water, resulting in an emulsion. Those active substances which are present in the solid form can first be liquefied together with the compound of the formula I. To this solution are then added the remaining components which are not soluble in water, and this mixture is then emulsified in water.

It is advantageous to combine the various phases slowly at room temperature or at increased temperature, for example at temperatures between 10° and 60° C., with continuous stirring using customary stirrers. This results in a finely divided emulsion. Aftertreatment of the emulsion which forms is not necessary, but can be carried out if desired.

The formulations according to the invention can be applied either in the prepared form or after having been diluted beforehand. The application rate depends on the concentration of the active substances in the emulsion and on the particular indication.

The emulsions according to the invention are employed using customary methods, for example by spraying, atomizing or watering. The formulations according to the invention are particularly suitable for those agrochemical preparations in which the aqueous formulation is applied undiluted or only slightly diluted with water.

In particular, these preparations are seed-dressing agents of herbicides, fungicides, insecticides, acaricides, gametocides, nematicides, rodenticides, growth regulators or of safeners (safeners are substances which have a protective effect on crop plants).

In total, the formulations according to the invention are distinguished by a series of advantages:
no formation of crystals
these emulsions remain physically unchanged on long-term storage at between −10° C. to +54° C.,
no organic solvents,
high flash point of the emulsions,
no unpleasant odour caused by organic solvents,
emulsions are simple to prepare,
well tolerated by plants and seed,
no adverse influence of the degree of effectiveness of the agrochemical active substance.

The advantages mentioned above, which generally apply to the formulation type according to the invention, are particularly important for application of seed-dressing agents.

In particular, it has emerged that seed treated with the formulation according to the invention has a high germination rate compared with the untreated control. The formulations according to the invention can therefore be employed in a particularly advantageous manner as seed-dressing agents.

The term seed is understood as meaning generative parts of plants which can be employed for propagating the crop plant. They include, for example, grains of seed (seed in the narrow sense), roots, fruits or tubers.

However, seed-dressing agents are mainly used for treating grains of seed. Grains of seed of the following plant species are particularly important:

Cereals (wheat, barley, rye, oats, rice, sorghum and related species); beet (sugar beet and fodder beet); pulse (beans, lentils, peas, soya beans); oil crops (oilseed rape, mustard, poppy, olives, sunflowers, coconuts, castor, All formulations 1 to 29 contain water in the respective amount to make up to 100% by weight.

Emulsifier 1 is calcium dodecylbenzenesulphonate, emulsifier 2 is an n-butanol/propylene oxide/ethylene oxide block polymer; percentage by weight of propylene oxide 44%, percentage by weight of ethylene oxide 54%.

TABLE 1

| Formulation No. | 1 | 2 | 3 | 4 | 5 | 6 | 7 | 8 | 9 | 10 | 11 |
|---|---|---|---|---|---|---|---|---|---|---|---|
| Furathiocarb % | 50,0 | 50,0 | 50,0 | 50,0 | 50,0 | 50,0 | 50,0 | 50,0 | 50,0 | 50,0 | 50,0 |
| Emulsifier 1 % | 0,4 | 0,4 | 0,4 | 0,4 | 0,4 | — | — | 0,4 | 0,4 | — | — |
| Emulsifier 2 % | 0,6 | 0,6 | 0,6 | 0,6 | 0,6 | — | — | 0,6 | 0,6 | — | — |
| Mono-sec-butylphenol % | 10,0 | 15,0 | — | — | — | — | — | — | — | — | — |
| Di-sec-butylphenol % | — | — | 10,0 | 15,0 | 20,0 | — | — | — | — | — | — |
| Tri-sec-butylphenol % | — | — | — | — | — | 10,0 | 15,0 | 10,0 | 15,0 | — | — |
| Oleyl alcohol % | — | — | — | — | — | — | — | — | — | 25,0 | 30,0 |

| Formulation No. | 12 | 13 | 14 | 15 | 16 |
|---|---|---|---|---|---|
| Furathiocarb % | 50,0 | 50,0 | 50,0 | 50,0 | 50,0 |
| Mono-n-nonylphenol % | 5,0 | 10,0 | 15,0 | — | — |
| n-Nonylphenol 98,9% Na-n-Nonylphenolate 1,1% | — | — | — | 10,0 | 15,0 |

| Formulation No. | 17 | 18 | 19 | 20 | 21 | 22 | 23 | 24 | 25 |
|---|---|---|---|---|---|---|---|---|---|
| Furathiocarb % | 50,0 | 50,0 | 50,0 | 50,0 | 50,0 | 50,0 | 50,0 | 50,0 | 50,0 |
| Di-n-nonylphenol % | 10,0 | 15,0 | 10,0 | — | — | — | — | — | — |
| Emulsifier 1 % | — | — | 0,4 | — | 0,4 | — | — | — | — |
| Emulsifier 2 % | — | — | 0,6 | — | 0,6 | — | — | — | — |
| n-Octylphenol % | — | — | — | 10,0 | 10,0 | — | — | — | — |
| n-Dodecylphenol % | — | — | — | — | — | 10,0 | 15,0 | — | — |
| n-Dodecylphenol 98,6% Na-n-Dodecylphenolate 1,4% | — | — | — | — | — | — | — | 10,0 | 15,0 |

| Formulation No. | 26 | 27 | 28 | 29 |
|---|---|---|---|---|
| Furathiocarb % | 50,0 | 50,0 | 50,0 | 50,0 |
| Trimethyl-styrylphenol 97,6% Trimethyl-styrylphenol 2,4% | 15,0 | 10,0 | — | — |
| Trimethyl-styrylphenol % | — | — | 15,0 | 10,0 | peanuts); the gourd family (pumpkin, cucumbers, melons); fibre plants (cotton, flax, hemp, jute); vegetables (spinach, lettuce, asparagus, cabbage species, carrots, onions, tomatoes, potatoes, paprika); or maize; and also ornamental plants and grasses. The seeds of maize and sugar beet are preferably treated.

The invention also relates to a process for dressing seeds using the aqueous formulations according to the invention, and to the treated seeds.

EXAMPLE 1

The formulations listed in the tables below are prepared by mixing the active substance furathiocarb at 40° to 50° C. with the compounds of the formula I and, if desired, other emulsifiers. The homogeneous solution which forms is then emulsified in the required amount of water in the course of 2 to 4 minutes, with stirring. When the addition is complete, stirring is continued for 5 minutes. This gives slightly coloured, viscous emulsions. These emulsions are stored at 20° C. or −5° C. to +54° C., and their stability is monitored.

Formulation Examples 1 to 29 give recipes where crystallization of the active substance does not occur during storage for six months. If the compound of the formula I is omitted in the formulations of Examples 1 to 29, the active substance crystallizes after only a few days.

EXAMPLE 2

Treatment of sugar beet seeds 1 kg of sugar beet seeds, cultivar KWS Kawevera, are dressed with 40 g of an aqueous formulation of the following composition:
50% of furathiocarb
15% of tri-sec-butylphenol
5% of 1,2-propylene glycol
30% of water The formulation is applied to the seed in a seed-dresser by means of a broadcasting disc, and mixing is continued for 2 minutes so that uniform distribution is achieved.

In comparison experiments, analogous formulations are applied in the same manner to sugar beet seeds, but these formulations contain xylene or dioctyl adipate in place of 15% of tri-sec-butylphenol.

The germination rate of the treated seed is determined as follows: 4 batches of 25 grains are placed in a moist fluted filter which is then kept for 7 days in a germination cabinet (temperature=25° C., relative atmospheric humidity=95%, photoperiod 8 hours/day). After this, the number of germinated grains from a total of 100 grains per test is determined.

The following result is obtained in the experiment described in this example:

| | Germination rate in % |
|---|---|
| Control | 95 |
| Formulation with tri-sec-butylphenol | 93 |
| Formulation with xylene | 53 |
| Formulation with dioctyl adipate | 15 |

EXAMPLE 3

Treatment of maize seeds 1 kg of maize, cultivar Blizzard, is treated using 33 g of an aqueous formulation of the following composition:
30% of furathiocarb
6% of tri-sec-butylphenol
33% of tackifier (aqueous latex suspensions)
1.5% of emulsifier (anionic surfactant)
0.3% of antifoam (silicone oil)
0.2% of colorant (®Irgalit red)
29% of water The product is poured onto the seed in a drum mixer, and the contents of the mixer are immediately mixed thoroughly for 3 minutes. After this, 18 g of a mixture of talc and Na Al silicate in the ratio 2:1 and 1% of colorant are added, and mixing is continued for 5 minutes.

In comparison experiments, analogous formulations are applied to the maize seed in the same manner, but these contain cyclohexanone, xylene or dimethyl phthalate in place of 6% of tri-sec-butylphenol.

The germination rate of the treated seed is determined as described in Example 2. The following result is obtained in the experiment described in this example:

| | Germination rate in % |
|---|---|
| Control | 96 |
| Formulation with tri-sec-butylphenol | 99 |
| Formulation with cyclohexanone | 54 |
| Formulation with xylene | 31 |
| Formulation with dimethyl phthalate | 23 |

We claim:

1. A process for dressing seed which comprises treating seed with an aqueous seed treating formulation said formulation being essentially free of organic solvents and comprising 1 to 70% by weight of
   a) an agrochemically active substance selected from the group consisting of herbicides, fungicides, insecticides, acaricides, gametocides, rodenticides, nematicides, growth regulators and safeners said agrochemically active substance being soluble in water at 20° C. to an extent of less than 1% and being liquid or solid at room temperature, b) a compound of formula I $$R-O-M \qquad (I)$$

where
R is $C_{12}$–$C_{20}$alkyl; $C_{12}$–$C_{20}$alkenyl; 4-biphenylyl; or unsubstituted or substituted phenyl, said substituted phenyl being: phenyl which is disubstituted to trisubstituted by $\alpha$-methyl-benzyl or $\alpha$-methyl-4-methylbenzyl, or phenyl which is monosubstituted to trisubstituted by alkyl, the total number of carbon atoms in the alkyl groups being 1 to 18; and M is hydrogen; a cation equivalent of an alkali metal ion or alkaline earth metal ion; or, in the event that R is 4-biphenyl or unsubstituted or substituted phenyl, M can also be ammonium, monoethanolammonium or diethanolammonium; in an amount sufficient to effectively inhibit crystallization of the active substance or effectively inhibit emulsion break-up;
   c) optionally other agrochemically active substances and formulation auxiliaries; and
   d) water to make up the bulk of the formulation to 100% to result in a seed treating formulation.

2. A process according to claim 1, wherein the seed is treated with an aqueous formulation which contains a tackifier and, as the active substance, furathiocarb, or methidathion.

3. A process according to claim 1 wherein the seed is treated with an aqueous formulation according to claim 1 said aqueous formulation being an emulsion in which the agrochemically active substance is present in the oil-phase and said aqueous formulation comprising additionally a tackifier and 0.5–5% by weight of an emulsifier selected from the group consisting of non-ionic emulsifiers and anionic emulsifiers.

* * * * *